United States Patent [19]

Righi

[11] 4,182,050
[45] Jan. 8, 1980

[54] LAUNDRY APPARATUS AND DRYERS

[75] Inventor: Dante Righi, Città di Castello, Italy

[73] Assignee: Renzacci S.p.A., Città di Castello, Italy

[21] Appl. No.: 867,340

[22] Filed: Jan. 5, 1978

[30] Foreign Application Priority Data

May 16, 1977 [IT] Italy .................. 49428 A/77

[51] Int. Cl.² ............................ F26B 3/04; F26B 3/30
[52] U.S. Cl. .............................. 34/60; 34/4; 34/41; 68/13 R
[58] Field of Search ............... 34/4, 39, 41, 133, 60, 34/68; 250/504, 514; 68/13 R; 432/112, 114

[56] References Cited

U.S. PATENT DOCUMENTS

| 1,756,821 | 4/1930 | Groen | 34/4 |
| 2,137,376 | 11/1938 | Altorfer | 34/133 |
| 2,293,618 | 8/1942 | Nelligan et al. | 68/15 |
| 2,707,837 | 5/1955 | Robinson et al. | 34/133 |
| 2,752,694 | 7/1956 | McCormick | 34/60 |
| 2,827,276 | 3/1958 | Racheter | 34/60 |
| 3,203,110 | 8/1965 | Fuhring et al. | 34/76 |
| 3,877,152 | 4/1975 | Gorman | 34/4 |

Primary Examiner—John J. Camby
Assistant Examiner—Larry I. Schwartz
Attorney, Agent, or Firm—Schwartz, Jeffery, Schwaab, Mack, Blumenthal & Koch

[57] ABSTRACT

A washing machine having an outer tub, a perforate rotatable drum housed in the tub, and a timer for cycling the machine through a series of operating phases. The tub has an opening and a housing affixed to the outer surface of the tub such that a space adjacent the tub opening and communicating with the tub is provided. Ultraviolet lamps are positioned in the housing, a door is located on the housing for sealingly closing the tub opening, and the door is controllable between open and closed positions. The timer controls opening and closing of the door so that items in the drum may be irradiated.

4 Claims, 6 Drawing Figures

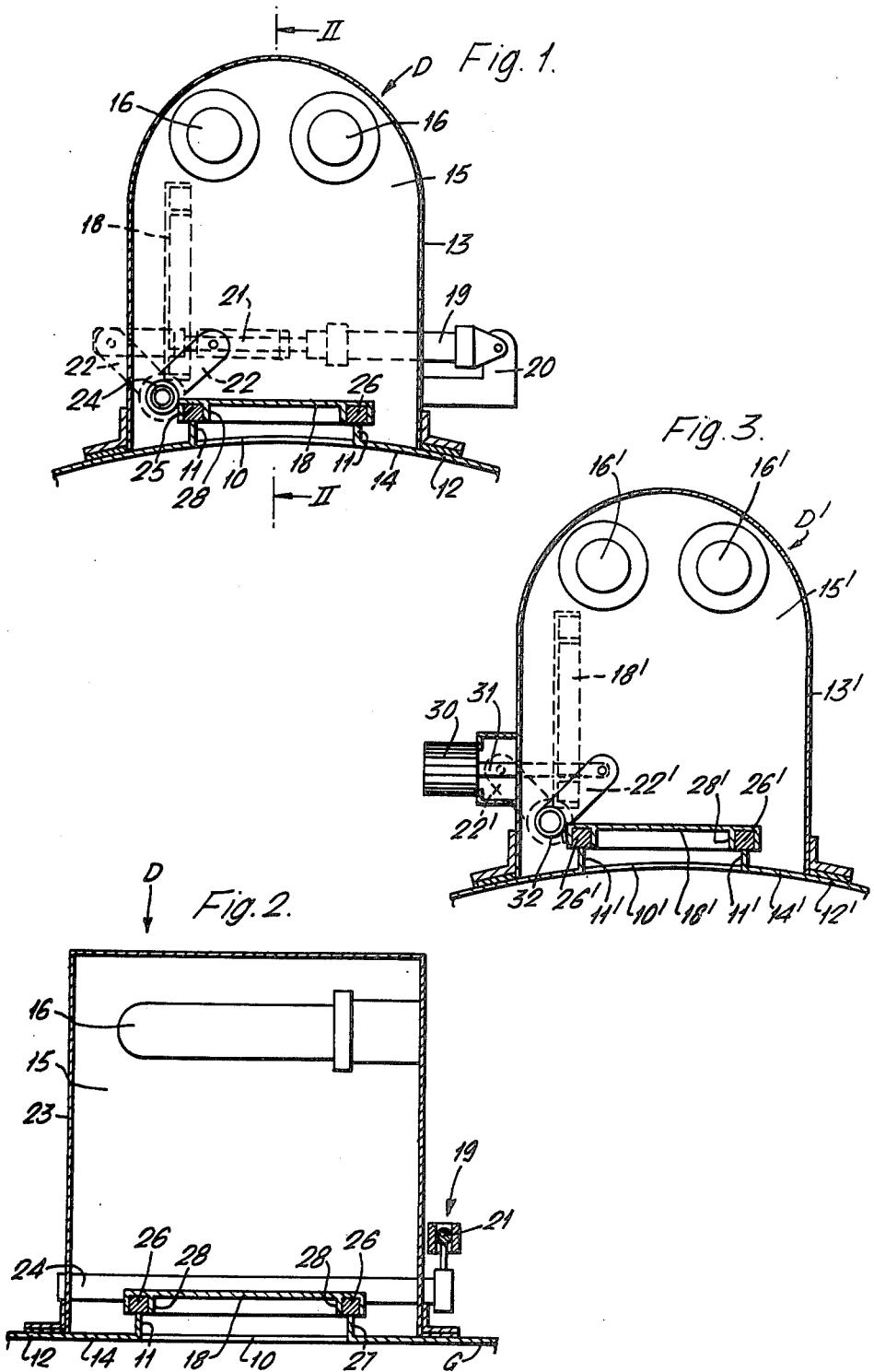

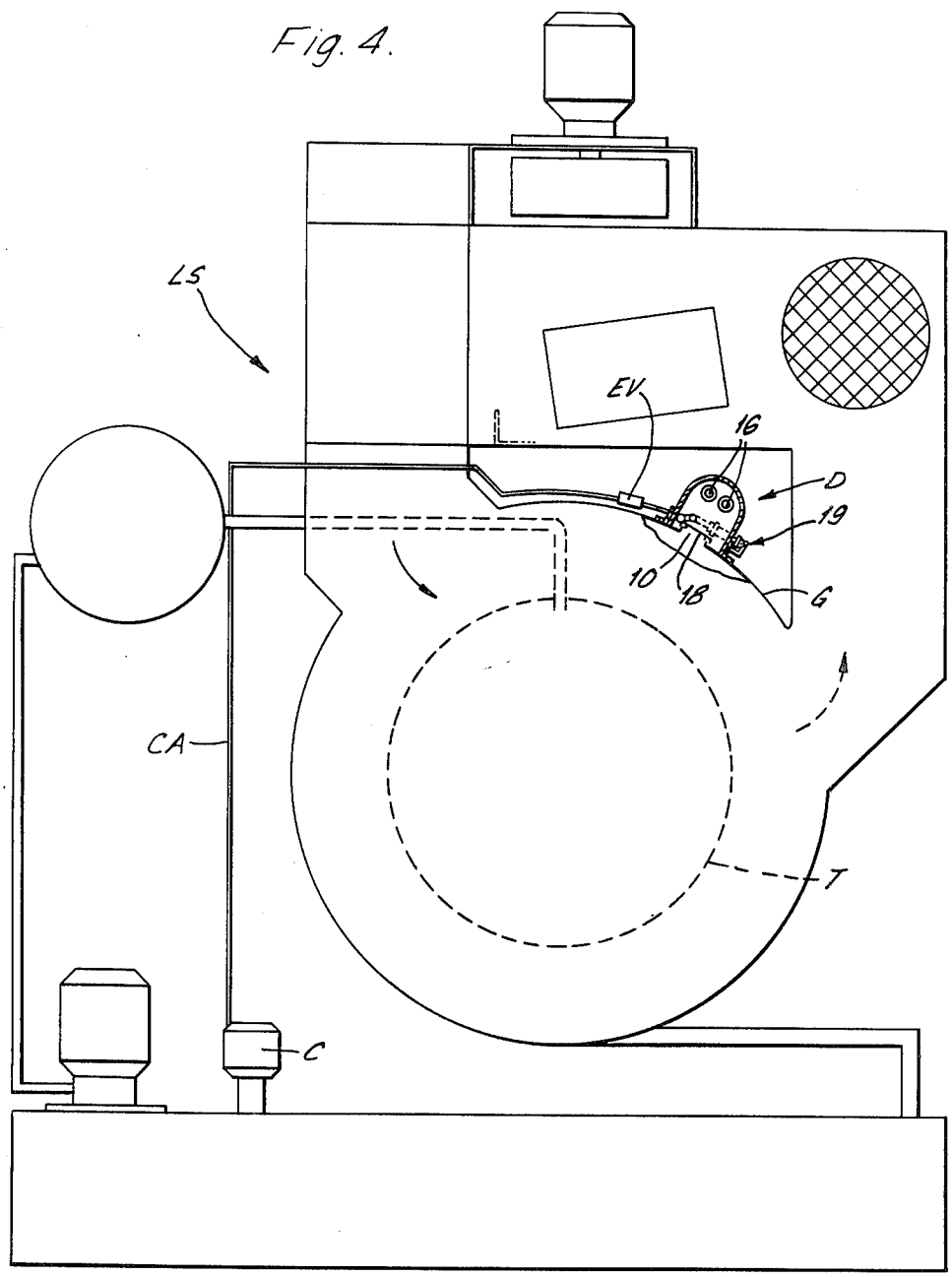

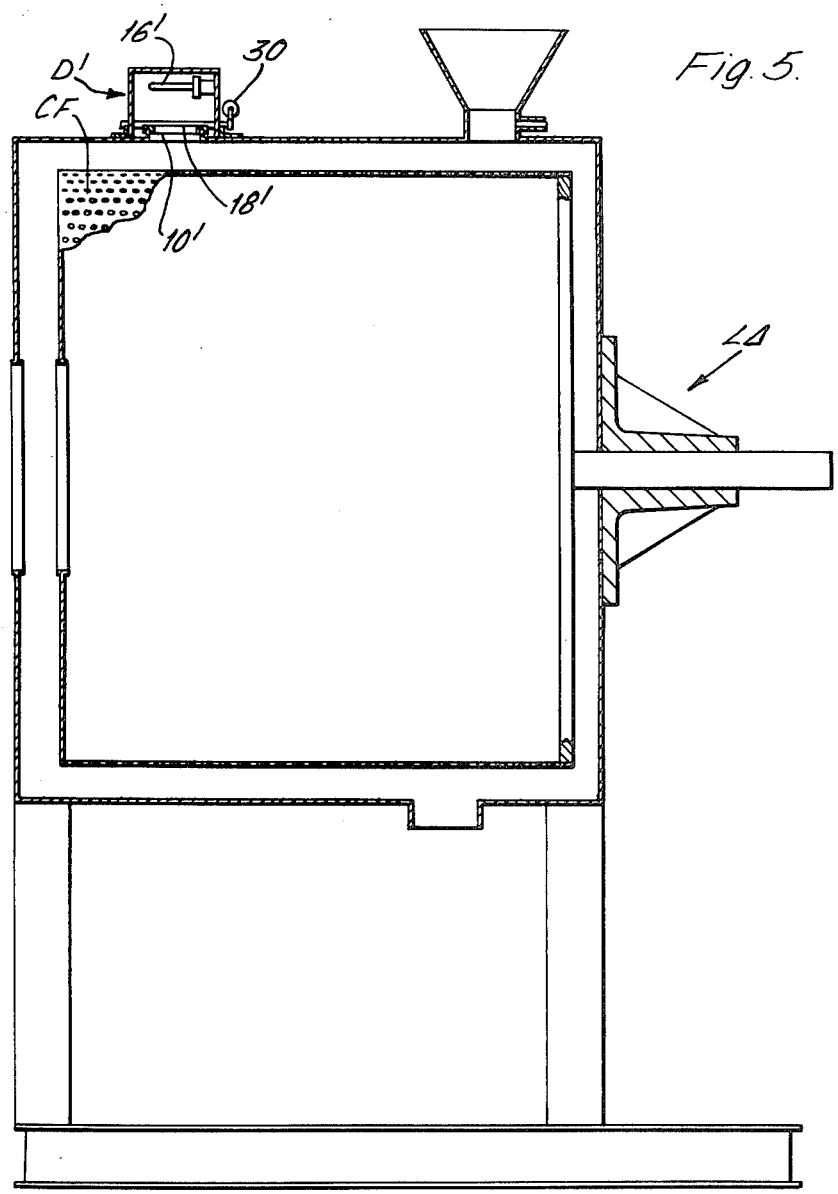

LAUNDRY APPARATUS AND DRYERS

This invention relates to an improvement in laundry apparatus, both of the industrial and of the domestic type, especially of the type where the treatment of clothing, linen and the like is performed. Dry-cleaning machines, washing machines, both for industrial and domestic use, and any type of dryers can be mentioned as examples of such apparatus.

According to the invention, in such apparatus for the treatment of clothing, linen, blankets and the like, which from now on will be generally called apparatus, a means exerting a disinfecting action is installed which is suitably connected to the timer of the associated apparatus with two possibilities: the operation thereof either is automatically controlled and included in the working cycle of the machine at any time, or this operation may be an independent and distinct cycle, manually and separately selectable on the timer.

The necessity of this improvement is self-evident; it will be useful, however, to point out the particular importance of applying the invention to apparatus utilized in laundries (as dry-cleaning machines) and to apparatus to be used in communities, mainly hospitals, hotels, and the like, where disinfection of the articles under treatment is of vital importance.

It is therefore a main object of the invention to provide apparatus, both for industrial and domestic use, adapted to wash and dry clothing articles provided with means exerting a disinfecting action thereon.

It is another object of the invention to provide such an apparatus, wherein the disinfecting phase can either be included in one or more working cycles thereof, so that it is automatically performed during a given cycle, or optionally form an independent and distinct cycle, manually and separately selectable on the timer.

Three possible embodiments of the invention are illustrated as non-restrictive examples and they are intended to be applied to dryers, laundry apparatus, for example for dry-cleaning laundries, where, as it is self-evident, clothes from different origins, and accordingly not infected clothes and infected clothes are frequently mixed together, since the apparatus need always work at full load, both for operating and economic reasons, and to washing machines, both of the domestic and of the industrial type, for which the same reasons as for dry-cleaning machines are true.

According to some presently preferred embodiments of the invention, a device is utilized comprising at least an ultraviolet lamp to disinfect the load of clothing and linen of the apparatus, the device being in such a position that the lamp (or lamps) can irradiate the load.

Such a solution presents the advantage that a double disinfecting action can be obtained by selecting lamps emitting an ultraviolet radiation of a selected wavelength since these lamps, besides the inherent disinfecting action of the ultraviolet rays determine a secondary disinfecting action due to the ozone generated by the radiation on the surrounding athmosphere.

As mentioned above, the disinfecting device comprising one or more ultraviolet lamps is connected to the timing circuit of the apparatus so that the device is operated either automatically by the timer at a selected time of any working cycle or manually controlling a suitable switch, independently of the apparatus cycles, as a distinct disinfecting cycle.

However, it is to be understood that other disinfecting means, similarly controlled either automatically or manually, can be utilized without departing from the scope of the invention.

Three embodiments of the invention will be now described in detail with reference to the annexed drawings, wherein:

FIG. 1 is an enlarged sectional view of a first embodiment of a device according to the invention, showing a detail of the lamp installation within an apparatus making use of cleansing agents and provided with an air compressor;

FIG. 2 is a sectional view along line II—II of FIG. 1;

FIG. 3 is a sectional view similar to FIG. 1, of a second embodiment of the invention;

FIG. 4 shows schematically the installation of a device according to the invention in association with a dry-cleaning machine;

FIG. 5 is a similar view relative to a washing machine; and

Figure 6:
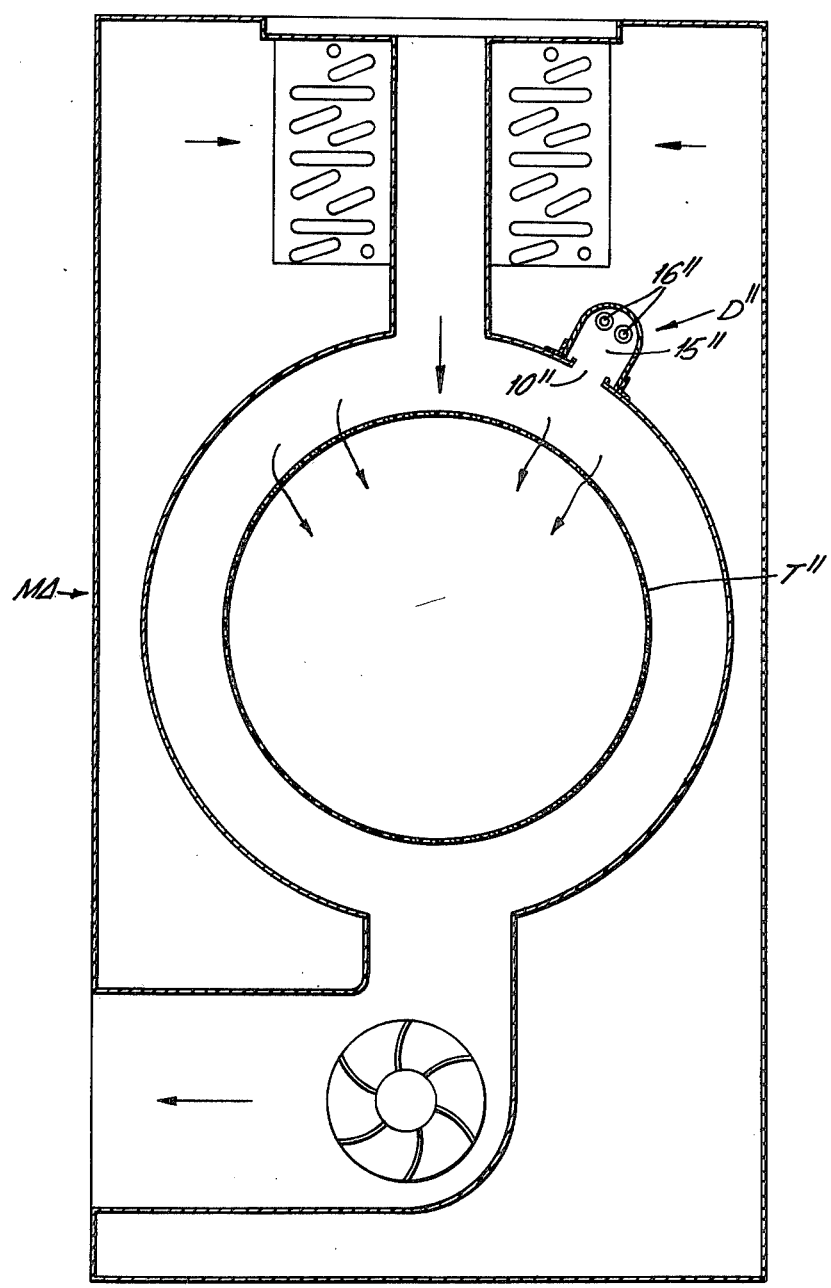
FIG. 6 is a similar view relative to a dryer.

In the application of the invention herein described and illustrated, the device for disinfecting the load, generally referred to with reference D, is shown within the casing thereof, which in turn can be suitably installed at any convenient point within the apparatus provided therefor.

FIGS. 1, 2 and 4 show the installation of device D within a laundry apparatus, such as dry-cleaning machines and some types of washing machines, provided with an air compressor.

In this embodiment, an elongated window 10, preferably of rectangular shape, having outwardly raided edges 11 is formed in tub G of the apparatus housing a rotating drum T which in turn contains the clothes to be treated in the apparatus. The base 12 of the casing of device D, generally referred to with reference 13, is sealingly fixed to the outer face of the tub, around window 10. Casing 13 and external portion 14 of tub G define a separate space 15 adjacent window 10 connected to tub G through window 10.

Two lamps 16 emitting a radiation of a frequency in the range of ultraviolet rays are mounted within the vault portion of casing 13, the lamps being placed to irradiate the space within tub G and then the load of clothes through window 10.

Since during the centrifuging phase the liquids in tub G are thrown against the walls thereof, during this phase window 10 is to be closed to protect lamps 16 and, accordingly, a closing door 18 is placed on wondow 10, the door being controlled to sealingly close this window when lamps 16 are off, door 18 being opened only upon energizing of the lamps.

In this embodiment, door 18 is controlled pneumatically utilizing air compressor C included in the apparatus, using a pneumatic cylinder unit 19, mounted externally of casing 13 on L-shaped support 20.

The end of piston rod 21 of cylinder unit 19 is connected to one end of a lever 22, the other end of which is integral with a shaft 24 supported by walls 23 of casing 13, edge 25 of door 18 being rigidly fixed to shaft 24.

It is to be pointed out that the perfect seal of door 18 against edges 11 is obtained by means of rectangular gasket 26 received within a groove defined between outer bent edge 27 of door 18 and inner bent edge 28, the sealing action of gasket 26 being obtained by pressing the gasket against the upper ridge of raised edge 11.

During operation of dry-cleaning machine LS, pneumatic cylinder unit 19 will be fed with compressed air from compressor C to maintain piston 21 in the retracted position, so that lever 22 connected thereto will hold door 18 in the closing position represented by full lines.

When the clothes are to be disinfected during the cleaning cycle, the apparatus timer (not shown) will suitably control solenoid valve EV on air supply pipe CA, which valve will allow the compressed air from compressor C to reach cylinder unit 19, so that piston 21 will reach the advanced position thereof, shown with dotted lines in FIG. 2, thus opening door 18 through lever 22.

Simultaneously, the apparatus timer will energize lamps 16 which will start irradiating the load of clothes through window 10 and the perforations of drum T alternately rotated within tub G.

The applicant presently thinks that the disinfecting phase will correspond to the drying phase of the apparatus and, more preferably, it will be performed during the last portion of the drying phase.

Upon ending of the disinfecting phase the timer will control the solenoid valve, so that piston 21 returns to the retracted position closing door 18 and will de-energize lamps 16.

It is to be pointed out that, as stated above, according to the invention the disinfecting phase comprising opening of door 18, energizing of lamps 16 and alternate rotation of drum T can be controlled optionally, independently of the apparatus cleaning cycle, either suitably setting manually the apparatus timer or by operating a suitable switch (not shown).

In FIGS. 3 and 5 an alternative device is shown, referred to with reference D', which is intended for installation on a washing machine LA, of the type unprovided with air compressor, where a pneumatic device for operating the door cannot be utilized advantageously.

As similarly illustrated and described with reference to FIGS. 1, 2 and 4, a rectangular window 10' with outwardly raised edges 11' is defined in tub G' of the apparatus, and base 12' of casing 13' of device D' is sealed around this window on the outer face of the tub, device D' similarly defining a separate space 15' communicating with tub G' through window 10'.

Lamps 16', received in the vault portion of casing 13' are also adapted to irradiate the interior of tub G' and then the linen within perforate basket CF, through window 10'.

Window 10' is closed by a door 18' having a portion 25' integral with w shaft 24' rotatably supported by walls 23' of casing 13'.

The above described components of device D' are substantially identical with the components of unit D, comprising a gasket 26' received between outer edge 28' and inner edge 28 and sealing the upper ridge of raised edge 11.

However, in absence of an air compressor closing and opening of door 18' are obtained electromagnetically by means of an electromagnet 30 mounted on the outer wall of casinf 13', the anchor 32 of which is connected to the end of lever 22' integral with shaft 24'.

The energizing of electromagnet 30 will cause door 18 to open through lever 22' while door 18' will close automatically upon de-energizing of electromagnet 30 due to torsion spring 32 which is mounted around shaft 24'.

Associated operation of apparatus and device D' will be evodently similar to that illustrated above with reference to FIGS. 1, 2 and 4, with the timer which energizes electromagnet 30 and lamps 16' upon starting of the disinfecting phase.

The disinfecting phase included in the washing machine working cycle is preferably performed after the centrifuging phase while basket CF is alternately rotated.

However, also in this case according to the invention it is possible to perform a disinfecting phase of the load in the apparatus, independently of the apparatus working cycle.

Finally, in FIG. 6 the installation is shown of a disinfecting device D" on a dryer MA.

In this apparatus, since the load is not centrifuged and detergents are not projected on the lamps, both closing door and relative control member are omitted. Thus, lamps 16" irradiate the load of linen which is drying within drum T" through an opening 10" without any door, with operation of the lamps which can occur during the drying cycle or at the end thereof.

It is to be understood that the means disinfecting the load during the disinfecting phase, herein illustrated as being two ultraviolet lamps, are not restricted to this example and, according to the invention, different disinfecting means or device can be comprised in the apparatus and they can be operated during the cycle thereof, for instance to cause the release in the tub or drum of appropriate disinfecting substances.

From the foregoing it is also evident that, according to the invention, any disinfecting means or device can be installed within the apparatus in any suitable position, without departing from the scope and concepts of the invention.

I claim:

1. In a machine for treating a load of cloth articles, said machine being a washing machine having an outer tub, a perforate rotatable drum housed in said tub for receiving said cloth articles, and a timer for cycling said machine through a series of operating phases, the improvement comprising:

an opening in said outer tub;

a housing having a lower opening larger than said tub opening and a base member affixed to said housing about the periphery of said housing opening, said housing sealingly affixed to the outer surface of said tub and located such that said housing opening and said tub opening are co-aligned, whereby said housing and a portion of the outer surface of said tub define a space adjacent said tub opening and communicating with said tub through said co-aligned tub and housing openings;

a pair of ultraviolet lamps for emitting radiation having a wavelength in the range from 2,000 to 3,000 Å, said lamps positioned in said housing such that said radiation passes through said co-aligned tub and housing openings and into said perforate rotatable drum;

a door located within said housing, one side of said door hingedly affixed at the periphery of said tub opening for movement between a closed position in which said door sealingly closes said tub opening and an open position in which said radiation may pass out of said housing through said tub and housing openings; and controllable means for moving said door between said open and closed positions;

said controllable means and said lamps coupled to said timer such that during at least a predetermined one of said operating phases said door is opened and said lamps are activated to emit said radiation, and during the remainder of said operating phases said door is closed.

2. The machine of claim 1, wherein said controllable means comprises an air compressor, a two-position pneumatic cylinder operatively connected such that said door is open when said cylinder is in a first position and closed when said cylinder is in a second position, and a solenoid valve coupled between said air compressor and said cylinder and responsive to said timer for actuating said cylinder.

3. The machine of claim 1, wherein said controllable means comprises an electromagnetic plunger assembly having a plunger operatively connected for opening and closing said door and a coil coupled to said timer.

4. The machine of claim 1, wherein said washing machine is a dry-cleaning machine.

* * * * *